Figure 1:
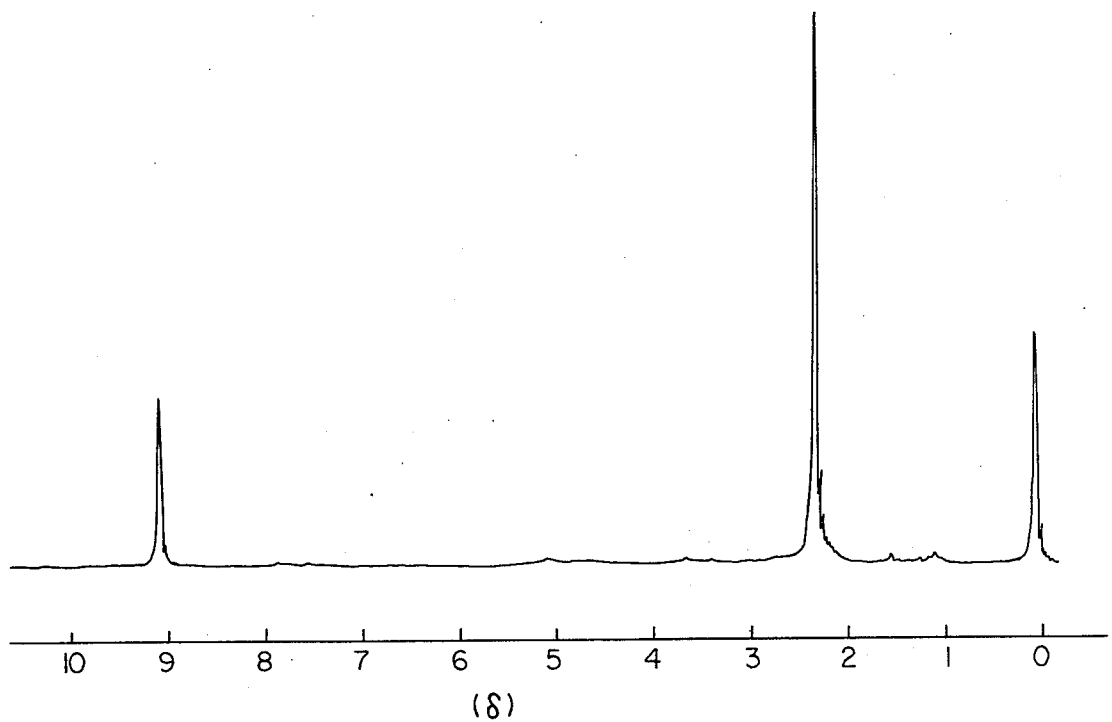

United States Patent [19]

Szent-Györgyi et al.

[11] 4,287,205

[45] Sep. 1, 1981

[54] HYPOTENSIVE AND ANALGESIC COMPOUNDS AND COMPOSITIONS AND METHODS FOR USING SAME

[75] Inventors: Albert Szent-Györgyi, Woods Hole, Mass.; Gabor B. Fodor, Morgantown, W. Va.

[73] Assignee: National Foundation for Cancer Research, Bethesda, Md.

[21] Appl. No.: 93,594

[22] Filed: Nov. 13, 1979

Related U.S. Application Data

[63] Continuation of Ser. No. 917,327, Jun. 20, 1978, abandoned.

[51] Int. Cl.³ .................. A61K 31/335; C07D 317/10
[52] U.S. Cl. ............................ 424/278; 260/340.9 R; 424/279; 424/285
[58] Field of Search ................................ 260/340.9 R

[56] References Cited

U.S. PATENT DOCUMENTS

| | | | |
|---|---|---|---|
| 3,048,598 | 8/1962 | Croxall et al. | 260/340.6 |
| 3,555,006 | 1/1971 | Storfer . | |
| 3,840,559 | 10/1974 | Hoffmann | 260/340.7 |
| 3,847,948 | 11/1974 | Yamamoto et al. | 260/340.3 |
| 3,944,509 | 3/1976 | Adams | 260/340.9 |
| 4,096,321 | 6/1976 | Weigele et al. | 536/120 |

OTHER PUBLICATIONS

Elliott et al., J. Med. Chem., 21(1): 112–114, (1978), Chem. Abstract-Chem. Index 88:2178.
Schönberg et al., Chem. Abstr. 35:6258[5], (J. Chem. Soc.), 1941: p. 348, (1941).
Chem. Abstr.: 86:2261, (1977).
Freireich et al., Cancer Chemother. Rpt. 16: 183–186, (1962).
Mihich, Cancer Res. 23: 1375–1389, (1963).
Sartorelli et al., Biochem. Biophys. Acta 103, 174–179, (1965).
Otsuka et al., Cancer Res., 27, 1498–1499, (1967).

*Primary Examiner*—Ethel G. Love
*Attorney, Agent, or Firm*—Fidelman, Wolffe & Waldron

[57] ABSTRACT

Novel cyclic acetals of the general formulae:

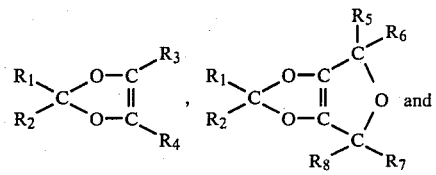

, 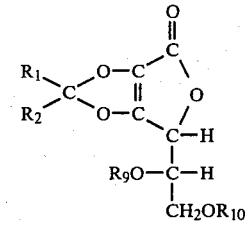 and
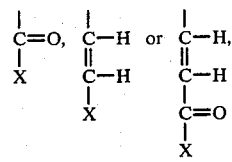

wherein $R_1$ is $$\begin{array}{ccc} | & | & | \\ C=O, & C-H & \text{or } C-H, \\ | & \| & \| \\ X & C-H & C-H \\ & | & | \\ & X & C=O \\ & & | \\ & & X \end{array}$$

wherein $R_2$ is hydrogen, alkyl, aryl or $R_1$,
wherein $R_3$ through $R_{10}$ are hydrogen, alkyl or aryl, wherein $R_5$ and $R_6$ together may form =O, wherein X is hydrogen, alkyl, cycloalkyl, aryl, hydroxyaryl or arylakyl, or wherein $R_8$ is

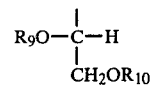

are described. Said compounds are prepared by mixing approximately equimolar amounts of the appropriate aldehyde or ketone, and enediol compound, and allowing same to react in aqueous solution under a nitrogen atmosphere.

Compositions containing these novel compounds exhibit hypertension and analgesic properties and are useful in the treatment of hypertension and pain in animals and humans.

17 Claims, 5 Drawing Figures

HYPOTENSIVE AND ANALGESIC COMPOUNDS AND COMPOSITIONS AND METHODS FOR USING SAME

This is a continuation of application Ser. No. 917,327, filed June 20, 1978, now abandoned.

BACKGROUND OF THE INVENTION

The present invention relates generally to novel chemical compositions, a process for preparing them, and use of these compositions as hypotensive and analgesic agents.

Briefly, the compositions are prepared by mixing one part aldehyde or ketone with one part enediol compound and allowing the mixture to react in aqueous solution for about one hour at room temperature. Following purification and sterilization, the composition is administered to animals or humans. Patients experience a general loss of pain and a decrease in blood pressure.

U.S. Pat. No. 2,927,054 discloses the condensation of certain sugars, e.g., glucose, mannose, fructose, etc., with an aldehyde or ketone to form cyclic acetals of the sugar. The mechanism apparently involves the elimination of water by union of the oxygen of the carboxyl group of the aldehyde or ketone and the hydrogen from each of two hydroxyl groups of the sugar. This condensation reaction proceeds upon heating the mixture to the boiling point of the aldehyde in the presence of an acid acetalization catalyst, conditions favoring the open chain form of the sugar. The two adjacent carbon atoms of the cyclic acetal ring are adjacent carbons of the aliphatic chain of the sugar molecule. Several of such cyclic acetal rings may be formed on the same sugar molecule; forming poly-(cyclic acetals).

OBJECTS OF THE INVENTION

An object of the present invention is to provide novel compounds having hypotensive and analgesic activity.

Another object of this invention is to provide novel compositions effective in the treatment of hypertension, and in the relief of pain, and methods for the application of such compositions.

Still another object is to provide a process for preparing the novel compounds discussed herein.

A still further object of this invention is to perform the reaction of the aldehydes (or ketones) and enediol compounds of the invention in aqueous media.

Other objects, advantages and novel features of the present invention will become apparent from the following detailed discussion.

The description of the novel invention described herein includes reference to the following figures:

FIG. 1 presents a nuclear magnetic spectrum (NMR) of pure methylglyoxal.

Figure 2:
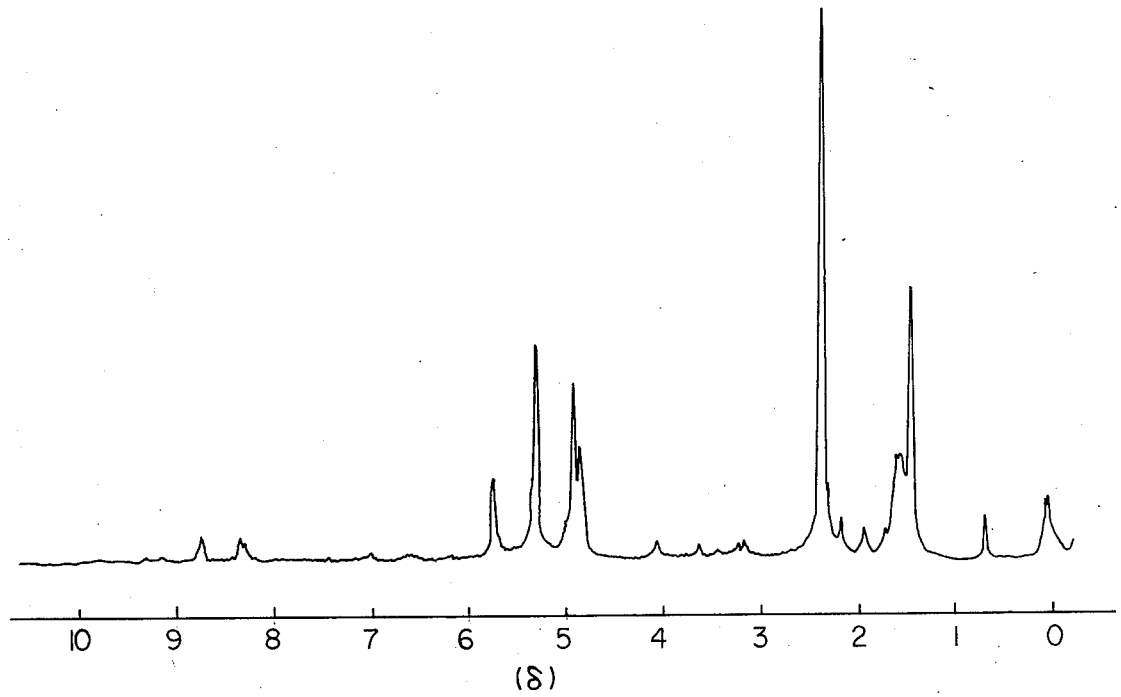

FIG. 2 presents an NMR spectrum of deuterium oxide solvated methylglyoxal.

Figure 3:
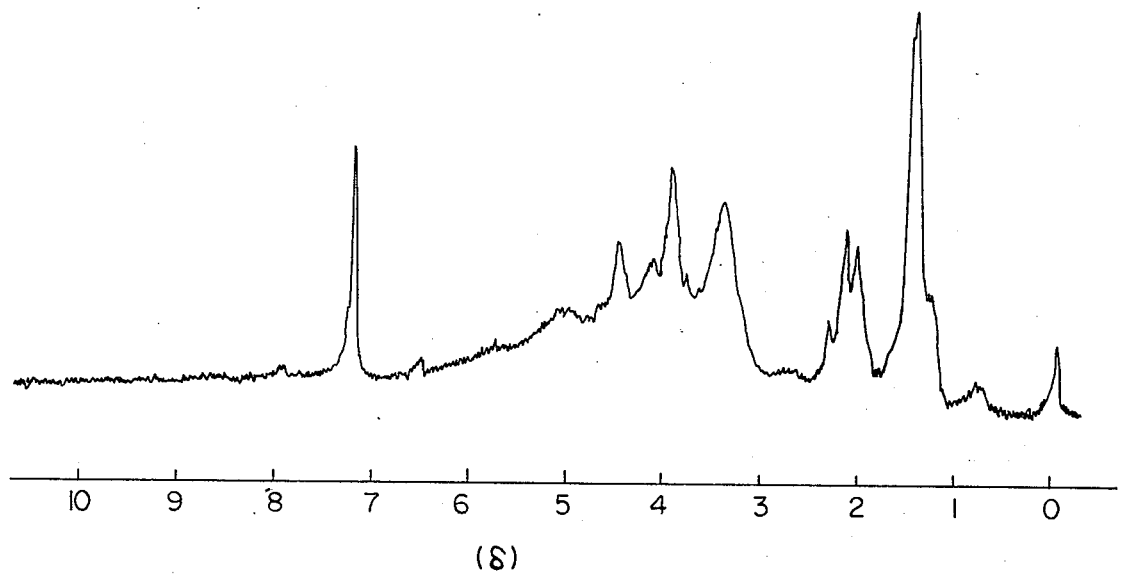

FIG. 3 presents an NMR spectrum of the product (in acetone-$D_6$) of the reaction between L-ascorbic acid and methylglyoxal.

Figure 4:
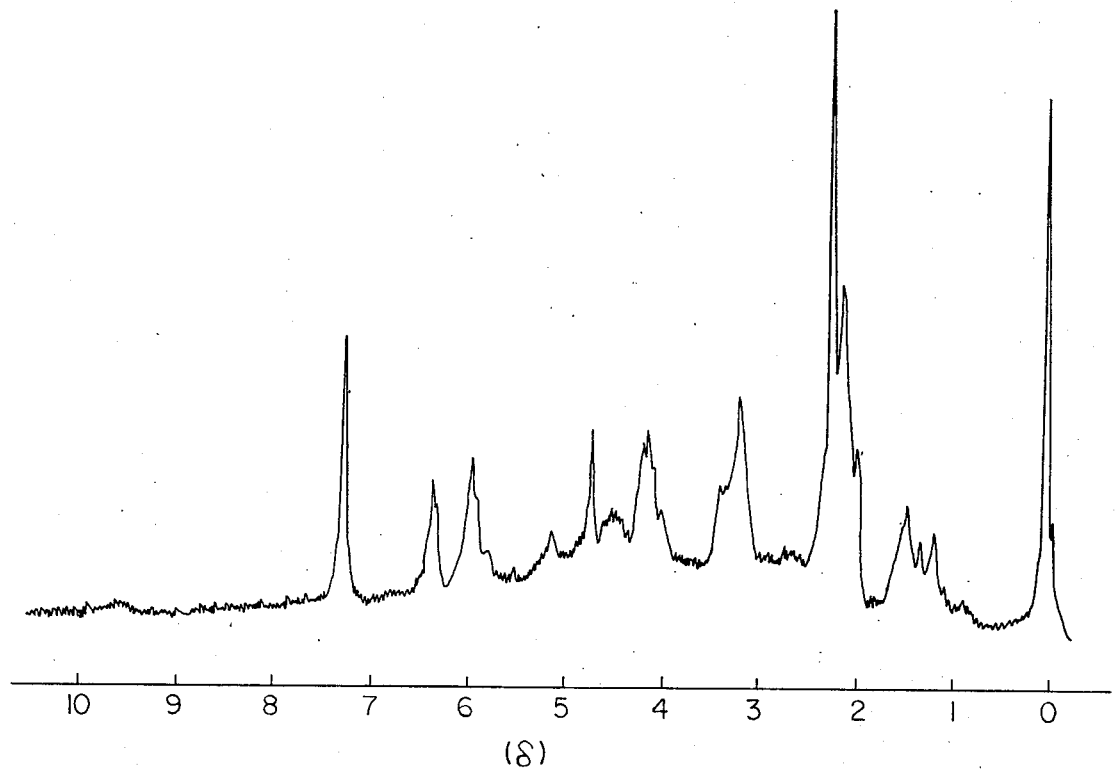

FIG. 4 presents an NMR spectrum of the product of Example 3.

Figure 5:
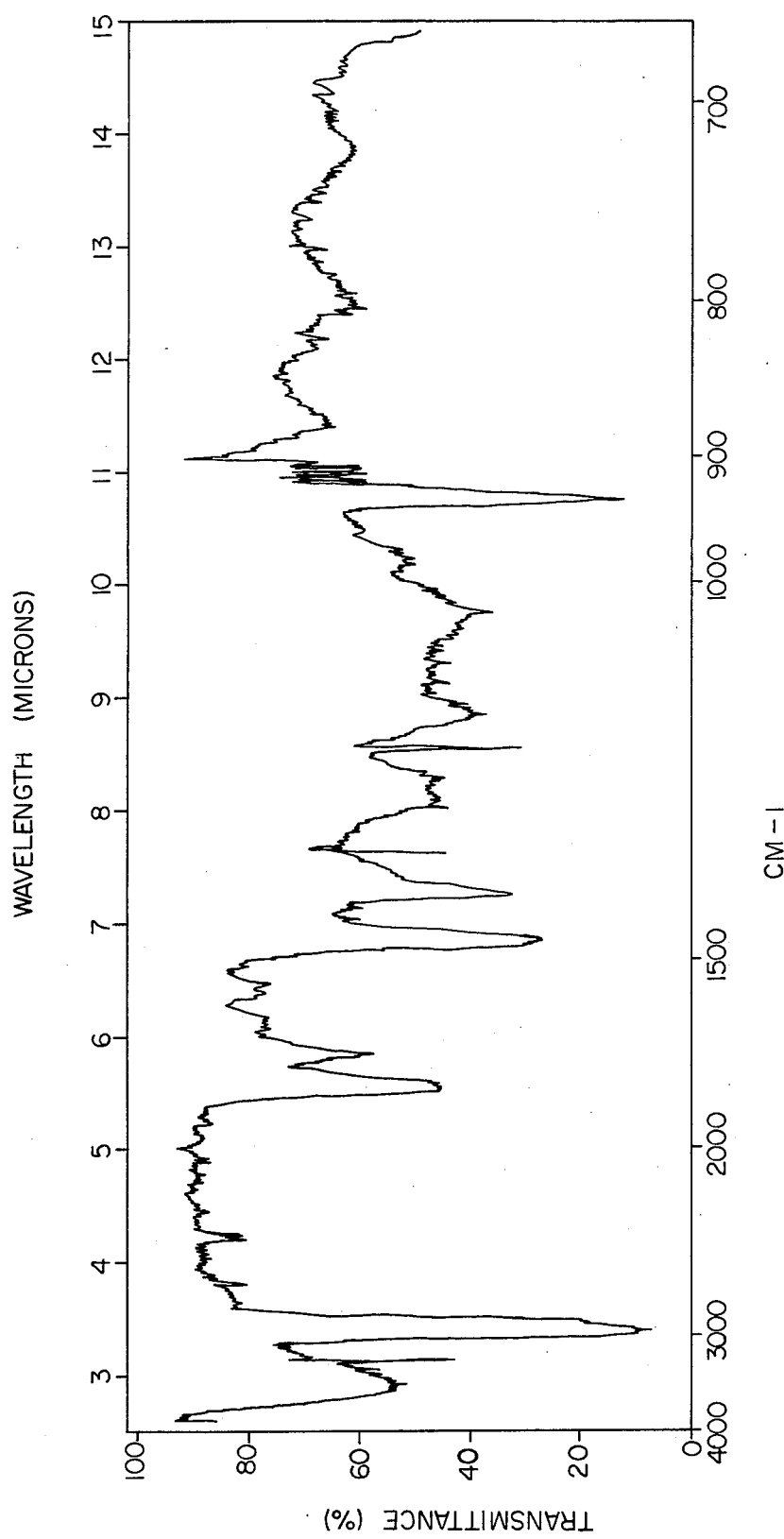

FIG. 5 presents an infrared spectrum of the product of Example 3.

DESCRIPTION OF THE INVENTION

The novel compounds of the instant invention are produced by mixing approximately equal amounts of an aldehyde or ketone of the general formula

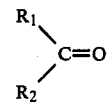

wherein $R_1$ is selected from the group consisting of

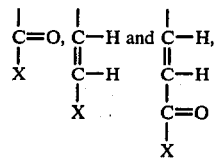

wherein X is hydrogen, alkyl, cycloalkyl, aryl, hydroxyaryl or arylalkyl,
wherein $R_2$, alkyl, aryl is hydrogen or $R_1$,
and an enediol compound of the general formula:

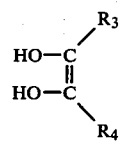

wherein $R_3$ and $R_4$ are hydrogen, alkyl, or aryl, or wherein $R_3$ and $R_4$ of the enediol reactant together form

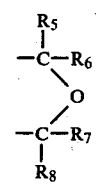

wherein $R_5$ through $R_8$ are hydrogen, alkyl, or aryl, wherein $R_5$ and $R_6$ together may form =O, and wherein $R_8$ may be

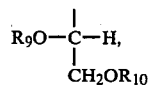

wherein $R_9$ and $R_{10}$ are hydrogen, alkyl or aryl, and allowing them to react under a nitrogen atmosphere at about room temperature in aqueous media.

The novel cyclic acetals produced by the above-described process include

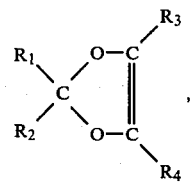

wherein $R_1$ is

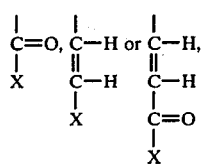

wherein X is hydrogen, alkyl, cycloalkyl, aryl, hydroxyaryl or arylalkyl,
wherein $R_2$ is hydrogen, alkyl, aryl or $R_1$, and
wherein $R_3$ and $R_4$ are hydrogen, alkyl or aryl.

The novel cyclic acetals of the instant invention also include the cases wherein $R_3$ and $R_4$ together form

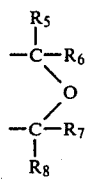

wherein $R_5$, $R_6$, $R_7$ and $R_8$ are hydrogen, alkyl or aryl.

Additional products of the invention include cases wherein $R_5$ and $R_6$ above together form —C=O, and wherein $R_8$ above is

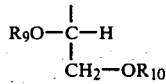

wherein $R_9$ and $R_{10}$ are hydrogen, alkyl or aryl.

Furthermore, this invention contemplates the hydrated form(s) of the above novel compounds.

DETAILED EMBODIMENT

In the case where the reactants are purified methylglyoxal and L-ascorbic acid, reaction is indicated by a decrease in the reducing character of L-ascorbic acid with iodine to about 5% of its original value. The purified reaction product is obtained by evaporation in vacuo followed by column chromatography or azeotropic distillation. The hydrated product will be referred to as AM.

It should be noted that purified methylglyoxal may be substituted with commercially available methylglyoxal, with or without polymerization inhibitors, which may contain hydrated or oligomeric methylglyoxal.

Nuclear magnetic resonance (NMR) spectra were obtained for pure methylglyoxal (FIG. 1), deuterium oxide solvated methylglyoxal (FIG. 2), and AM monohydrate (FIG. 3). An infrared (IR) spectrum of AM monohydrate was also obtained. The NMR spectrum showed two different methyl-proton resonances, one expected for a methylketone (at $\delta 2.2$) and a second that can be attributed to a hydrated methylketone (at $\delta 1.8$). Comparing FIGS. 2 and 3, one notes that the absorption due to the aldehydic proton of methylglyoxal appears to have shifted to the acetal region ($\delta 4.0$–4.5). Integration indicates a 1:1 (or 4:4) ratio of total ascorbic acid to total methylglyoxal C—H protons.

From this data one may infer that the enolic hydroxyls (at positions 2 and 3) of ascorbic acid reacted with the aldehyde carboxyl group of methylglyoxal to form a cyclic acetal as follows:

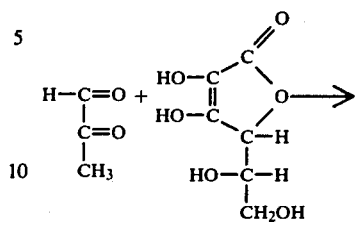

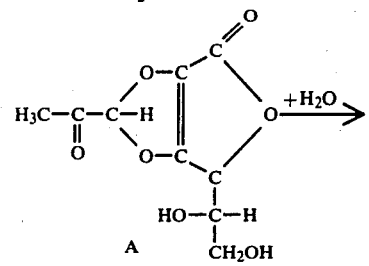

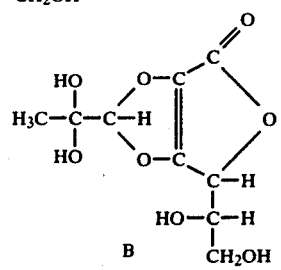

The ketonic carbonyl of structure A undergoes hydration (to the extent of about 90%) to form the product of structure B. The invention is not limited to any particular reaction mechanism. The reaction may proceed through reaction between methylglyoxal monohydrate and L-ascorbic acid, or between methylglyoxal and L-ascorbic acid which product is then hydrated.

Elemental analysis of the product (AM) gave C, 43.91%; H, 5.93%; O, 51.16% (O determined indirectly). $C_9H_{12}O_8$ requires C, 43.55%; H, 4.84%; O, 51.61%.

Similar NMR and IR analyses were performed on compounds produced from other aldehydes or ketones contemplated by this invention substituted for methylglyoxal, and on compounds produced from other enediol compounds substituted for L-ascorbic acid. In all such cases, the NMR and IR spectra were consistent with the product being a cyclic acetal.

It should be noted that it is surprising and unexpected that the reactions of the instant invention proceed in aqueous solution. It is generally known and expected in this field of organic chemistry that acetalization and ketalization reactions occur in anhydrous media. In addition, it is unexpected that the aldehydes and ketones discussed herein react selectively at the 2,3 hydroxyls of L-ascorbic acid, since all known acetals of L-ascorbic acid are formed by the 5,6-hydroxyl groups.

EXAMPLE 1

100 grams of L-ascorbic acid were dissolved in 400 milliliters (ml) of oxygen-free distilled water in a nitrogen atmosphere. 205 ml of methylglyoxal (40% aqueous solution, available from Aldrich Chemical Co., Inc., Milwaukee, Wisconsin) were added to the L-ascorbic acid solution and the mixture was allowed to stand at room temperature under a nitrogen atmosphere for about one hour. After flushing the flash evaporator with nitrogen, the mixture was water evaporated to constant weight at room temperature to a pale yellow sticky mass and yielded 130 grams. This product was spotted on thin layer chromatographic plates of cellulose and placed in a chamber containing ethyl acetate:benzene (2:3) as solvent. Methylglyoxal ascended with the solvent front. The product had an Rf value of about 0.3 and ascorbic acid did not move.

When titrated with iodine solution the product showed the presence of 5% ascorbic acid or its equivalent reducing substance.

EXAMPLE 2

1.52 grams (0.01 mole) of phenylglyoxal monohydrate were added to a solution of 1.76 grams (0.01 mole) of L-ascorbic acid in 50 ml water and kept stirring under a nitrogen atmosphere for one hour after which it was evaporated in vacuo to dryness. (Alternatively, it may be freeze-dried.) The product was isolated as in Example 1. The NMR spectrum of the major product showed absorption around $\delta 4.0$–$4.5$, characteristic of the acetal C—H. The infrared (IR) spectrum showed two distinct carbonyls, one of a lactone and another of an aroyl carbonyl group. There was about 50% iodine consumption upon titration which indicates the partial reaction of the free enediolic group.

EXAMPLE 3

2-methyl-2,5-dimethoxy-2,5-dihydrofuran (2,5-dimethoxy, 2,5-dihydro sylvan) was synthesized as described by Clauson-Kaas and Limborg (Clauson-Kaas, N., and F. Limborg, *Act. Chem. Scand.*, 1:619 (1977)). 10 grams of this material were added to an aqueous solution of L-ascorbic acid (5 grams/25 ml water) under a nitrogen atmosphere. A pale yellow solution was obtained after 10 minutes. Water was removed by overnight vacuum evaporation at room temperature. There was no iodine consumption upon titration indicating that the 2,3-hydroxyls of L-ascorbic acid had reacted. The crude product showed two spots (Rf 0.65 and 0.3) on silica gel thin layer chromatographic plates using a chloroform::methanol (9:1) solvent.

A 60 megahertz NMR spectrum (FIG. 4) in acetone-d₆ indicated the presence of

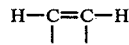

(vinyl),

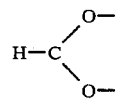

(acetal) and

(methyl carbonyl) protons in addition signals for the C₄, C₅ and C₆ L-ascorbic acid protons. The IR spectrum (in nujol mull; FIG. 5) indicated the presence of several hydroxyl groups and two distinct carbonyl groups.

EXAMPLE 4

Using the same experimental techniques as outlined in Example 2, 5.6 grams (0.1 mole) of acrolein were added to an aqueous solution (20 ml) of 20 grams of L-ascorbic acid. As soon as the oily acrolein disappeared a colorless precipitate of the monoacetal separated. It was filtered off and characterized in the usual way as the 2,3-monoacetal of L-ascorbic acid with acrolein.

EXAMPLE 5

The yellow product obtained as described in Example 1 was dissolved in a small amount of ethyl acetate::benzene (2:3) and applied to a chromatographic column containing DEAE-cellulose (diethylaminoethyl cellulose) adsorbent material. A narrow band of the yellow product slowly moved down the column as ethyl acetate:benzene (2:3) solvent was passed through the column. The product was collected in a small volume of filtrate.

EXAMPLE 6

The yellow product obtained as described in Example 1 was dissolved in a small amount of ethyl acetate and adsorbed on Celite (siliceous or diatomaceous earth) and dried. The dried Celite powder was washed with chloroform to remove excess methylglyoxal. Product was then removed from the Celite by elution with ethyl acetate.

EXAMPLE 7

13 grams of the yellow product obtained as described in Example 1 was dissolved in 200 ml of ethyl acetate and the solvent evaporated at room temperature. Excess methylglyoxal was removed as an azeotropic mixture. (Alternatively, chloroform or water may be substituted for ethyl acetate). Methylglyoxal in ethyl acetate was estimated by precipitation as the 2,4-dinitrophenylhydrazone and was found to be about 8%.

Further studies of the product purified by the methods of Examples 5 or 6 followed by evaporation showed:

(a) that the product is hygroscopic and tends to form an amorphous mass;

(b) that the product contains 5 to 8% ascorbic acid (on the basis of iodine consumption); and (c) that, upon reaction with excess 2,4-dinitrophenyl hydrazine, the 2,4-dinitrophenyl hydrazone of methylglyoxal forms over a period of 4–5 days.

The estimation of 2,4-dinitrophenyl hydrazones suggests a 1:1 molar combination of L-ascorbic acid and methylglyoxal in the product.

EXAMPLE 8

The procedures of Examples 1 and 5 were followed using freshly distilled methylglyoxal. The product after chromatographic purification was a colorless white powder which was less hygroscopic than the product of Example 5.

EXAMPLE 9

0.25 ml of a 2.5% aqueous solution of the product of Example 6 was administered intraperitoneally (i.p.) twice daily to Swiss albino mice (25 grams each). No toxic symptoms were observed.

A single injection per day of 0.25 ml of a 5.0% aqueous solution of the product of Example 7 produced a loss of weight, diarrhea and eventually death.

EXAMPLE 10

Twenty Swiss albino mice (25 grams each) were injected with $4 \times 10^6$ cells of Ehrlich carcinoma. Another 20 animals were injected similarly with $4 \times 10^6$ Sarcoma 180 cells. On the following day half of the animals received two injections (i.p.) of 0.25 ml of a 2.5% aqueous solution of the product of Example 7. The injections were repeated daily. On the eighth day the animals were sacrificed and the peritoneal cavity of each was washed with 20 ml of saline (0.9%). The washings were combined and centrifuged and the volume of the sediment was measured. This sediment contained the harvested malignant cells. Table I presents the results of summing the volumes of cells obtained from the peritoneal cavities of 20 mice. No loss of weight or toxic symptoms were observed except for slight hemorrhaging in the peritoneal cavity of animals receiving treatment.

TABLE I

| Cells Injected | Untreated | Treated |
|---|---|---|
| Ehrlich carcinoma | 1.27* | 0.14 |
| Sarcoma 180 | 1.46 | 0.05 |

*Sum of volumes of harvested cells, milliliters.

EXAMPLE 11

Seven patients having advanced stages of various forms of cancer were treated by oral administration of 250 mg four times daily in orange juice or by intravenous (I.V.) administration of 1 milligram AM/ml 0.9% saline to provide a total daily dose of 1 gram; a full clinical examination was carried out prior to administration. Constant observation with pulse, temperature and blood pressure control was maintained throughout infusion time.

PATIENT A: Female, Age 40

Histological Diagnosis: Undifferentiated carcinoma of (R) kidney with metastases.
Previous Treatment: Adriamycin, Cyclophosphamide, Vincristin, 5-Fluorouracil, Steroids, Warfarin Sodium. Three Courses given with partial remission after 1st and 2nd Courses only.
Status at Start of AM Therapy: Patient very ill, dyspneic, cough, abdominal and chest pain.
Dose: 1 gram (g) I.V. over 24 hours on Day 0; 1 g I.V. over 24 hours on Day 2; 1 g oral over 24 hours on Day 4, 5 and 8; 1 g I.V. over 24 hours on Day 15 to 21—Continuing.
Results: Marked clinical improvement in breathing within 12 hours. Pain free by 24 hours. Blood pressure fell steadily from start of 130/90 to 75/50 on Day 3. Day 15, I.V. restarted. No improvement in first 24 hours then gradual recovery over next 24 hours. Pain free and breathing normally.

PATIENT C: Female, Age 46

Histological Diagnosis: Intraduct Carcinoma of Breast. Stage IV. Bone metastases.
Previous Treatment: Cyclical combined chemotherapy with Cyclophosphamide, 5-Fluorouracil, Adriamycin and Methotrexate. Deep X-ray Therapy to spinal secondaries. RF. Hyperthermia.
Status at Start of AM Therapy: Liver and bone metastases. Severe pain. Relieved by morphine.
Dose: 1 g I.V. over 24 hours on Day 0 and 2.
Result: Pain free six hours after start of infusion. Return of pain for 12 hours after completion of Day 0 infusion. Repeat infusion again produced pain-free period for 24 hours after infusion. No toxic effects.

PATIENT D: Female, Age 43

Histological Diagnosis: Advanced undifferentiated carcinoma of breast with multiple metastases.
Previous Treatment: Deep X-ray Therapy. Cyclical chemotherapy. Warfarin Sodium. RF Hyperthermia.
Status at Start of AM Therapy: Bone, lung and liver secondaries. Back pain and dyspnea.
Dose: 1 gram I.V. in six hours on Day 0 and Day 7.
Result: Relief of pain and Dyspnea. No analgesics required since Day 0. Extremely tired. Blood pressure fell from 130/80 to 100/60 on Day 0. Recovered on Day 1 to 130/80. Fell again on Day 7, 130/90 to 100/70.

PATIENT E: Female, Age 40

Histological Diagnosis: Recurrent Melanoma. Metastatic.
Previous Treatment: B.C.G. Levamisole, D.T.I.C. Surgical excision—block dissection. R.F. Hyperthermia.
Status at Start of AM Therapy: Pain.
Dose: 1 g over six hours on Day 0. 1 g over six hours on Day 5. 1 g over six hours on Day 9.
Result: Pain-free by end of first infusion. Pain returned on Day 7 and 8. Vomiting after infusion on Day 5. Extreme tiredness Day 6 to Day 9. Blood pressure stable.

PATIENT F: Female, Age 53

Histological Diagnosis: Adenocarcinoma of breast with brain metastases. Recurrent.
Previous Treatment: Surgical resection of brain metastases. Cobalt irradiation therapy. Cylical combined chemotherapy.
Status at Start of AM Therapy: Miserable with headache and projectile vomiting. Pain.
Dose: 1 g I.V. over 24 hours on Day 0, 1, 2, 3, 4, 5, 6, 7, continuing.
Result: Vomiting stopped on Day 2. Pain decreased but present on twisting movement in lumbar area. Headache gone on Day 5. No side effects. Patient bright and cheerful on Day 7. Blood pressure maintained.

PATIENT G: Male, Age 73

Histological Diagnosis: Squamous Cell carcinoma of lung, inoperable. Chronic Bronchitis and emphysema.
Previous Treatment: Radiofrequency Hyperthermia.
Status at Start of AM Therapy: Karnofsky 0 deteriorating. Severe Dyspnea. Chest pain relieved by analgesics.
Dose: 1 gram I.V. in 24 hours.
Result: Nil except for relief of chest pain for 24 hours. Patient continued to deteriorate and died Day 3.

The above clinical studies establish that AM is useful in the treatment of hypertension and pain.

The mode of action of the compounds of the invention with respect to hypotensive and pain relieving activities is, at this point, unclear.

What is claimed is:

1. A compound of the formula

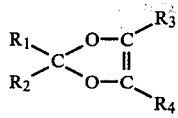

wherein $R_1$ is selected from the group consisting of

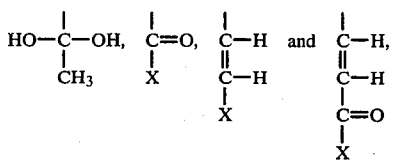

wherein $R_2$ is selected from the group consisting of hydrogen, alkyl, aryl and $R_1$, wherein $R_3$ and $R_4$ are selected from the group consisting of hydrogen, alkyl, and aryl, or wherein $R_3$ and $R_4$ together form

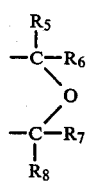

wherein $R_5$, $R_6$, $R_7$, and $R_8$ are selected from the group consisting of hydrogen, alkyl, and aryl, wherein $R_5$ and $R_6$ together may form =O, wherein $R_8$ may be

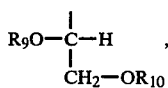

and wherein $R_9$ and $R_{10}$ are selected from the group consisting of hydrogen, alkyl and aryl, and wherein X is selected from the group consisting of hydrogen, alkyl, cycloalkyl, aryl, hydroxyaryl and arylalkyl.

2. A compound of claim 1, wherein $R_3$ and $R_4$ together form

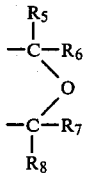

wherein $R_5$, $R_6$, $R_7$ and $R_8$ are selected from the group consisting of hydrogen, alkyl and aryl.

3. A compound of claim 2, wherein $R_5$ and $R_6$ together form =O, wherein $R_8$ is

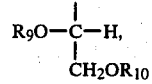

and wherein $R_9$ and $R_{10}$ are selected from the group consisting of hydrogen, alkyl and aryl.

4. The compound of claim 1, wherein $R_1$ is

and $R_2$ is hydrogen.

5. The compound of claim 2, wherein $R_1$ is

and $R_2$ is hydrogen.

6. The compound of claim 3, wherein $R_1$ is

and $R_2$, $R_9$ and $R_{10}$ are hydrogen.

7. The compound of claim 1, wherein $R_1$ is

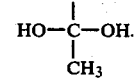

8. The compound of claim 2, wherein $R_1$ is

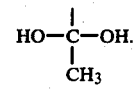

9. The compound of claim 3, wherein $R_1$ is

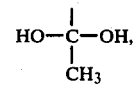

10. An analgesic composition comprising an effective amount of a compound of claim 1 for treating pain and a pharmaceutical carrier therefor.

11. A hypotensive composition comprising an effective amount of a compound of claim 1 for treating hypertension and a pharmaceutical carrier therefor.

12. An analgesic composition comprising an effective amount of a compound of claim 1 for treating pain dissolved in about 10 to 10,000 weight percent, based on the weight of said compound, of 0.9 percent saline.

13. An hypotensive composition comprising an effective amount of a compound of claim 1 for treating hypertension dissolved in about 10 to 10,000 weight percent, based on the weight of said compound, of 0.9 percent saline.

14. A method for treating pain in humans and animals comprising intravenous injection of the composition of claim 12.

15. A method for treating hypertension in humans and animals comprising intravenous injection of the composition of claim 13.

16. A method for treating pain in humans and animals comprising intraperitoneal injection of the composition of claim 12.

17. A method for treating hypertension in humans and animals comprising intraperitoneal injection of the composition of claim 13.

* * * * *